US008852179B2

(12) United States Patent
Ward et al.

(10) Patent No.: US 8,852,179 B2
(45) Date of Patent: Oct. 7, 2014

(54) APPARATUS, SYSTEM AND METHOD FOR MONITORING TISSUE DURING AN ELECTROSURGICAL PROCEDURE

(75) Inventors: Arlen K. Ward, Thornton, CO (US); Casey M. Ladtkow, Arvada, CO (US)

(73) Assignee: Covidien LP, Mansfield, MA (US)

( * ) Notice: Subject to any disclaimer, the term of this patent is extended or adjusted under 35 U.S.C. 154(b) by 1516 days.

(21) Appl. No.: 12/249,263

(22) Filed: Oct. 10, 2008

(65) Prior Publication Data
US 2010/0094271 A1    Apr. 15, 2010

(51) Int. Cl.
*A61B 18/18* (2006.01)
*A61B 18/14* (2006.01)
*A61B 5/00* (2006.01)
A61B 17/00 (2006.01)
A61B 5/01 (2006.01)
A61B 17/29 (2006.01)
A61B 5/053 (2006.01)

(52) U.S. Cl.
CPC ............. *A61B 18/18* (2013.01); *A61B 18/1445* (2013.01); *A61B 2017/00039* (2013.01); *A61B 5/0059* (2013.01); *A61B 18/1815* (2013.01); A61B 5/01 (2013.01); A61B 2018/1432 (2013.01); A61B 2017/2945 (2013.01); A61B 5/053 (2013.01)
USPC ............................................. 606/33; 604/41

(58) Field of Classification Search
CPC ............... A61B 18/1445; A61B 18/18; A61B 18/1815; A61B 2017/00039; A61B 2017/2945; A61B 2018/1432; A61B 5/0059; A61B 5/01; A61B 5/053
USPC ................................................. 606/34, 33, 41
See application file for complete search history.

(56) References Cited

U.S. PATENT DOCUMENTS

| D263,020 S | 2/1982 | Rau, III |
| 4,615,330 A | 10/1986 | Nagasaki et al. |
| D295,893 S | 5/1988 | Sharkany et al. |
| D295,894 S | 5/1988 | Sharkany et al. |
| 5,300,068 A | 4/1994 | Rosar et al. |

(Continued)

FOREIGN PATENT DOCUMENTS

| DE | 179607 | 3/1905 |
| DE | 1099658 | 2/1961 |

(Continued)

OTHER PUBLICATIONS

U.S. Appl. No. 12/244,873, filed Oct. 3, 2008.

(Continued)

*Primary Examiner* — Emily Schmidt
*Assistant Examiner* — Michael J Anderson

(57) ABSTRACT

A system for monitoring and/or controlling tissue modification during an electrosurgical procedure is provided. The system includes an electrosurgical apparatus adapted to connect to an electrosurgical generator. The electrosurgical apparatus configured to transmit energy to tissue. The system also includes a control system having one or more electromagnetic wave sources configured to generate the interrogator wave of one or more frequencies adjacent tissue. One or more sensors are configured to transmit and sense a reflected portion of the interrogator wave of at least one frequency to determine dielectric boundary data. A processor operatively coupled to the control system and to the electrosurgical generator configured to control the delivery of electrosurgical energy from the electrosurgical generator to tissue based on dielectric boundary data provided by the one or more sensors.

22 Claims, 8 Drawing Sheets

(56) References Cited

U.S. PATENT DOCUMENTS

| | | | |
|---|---|---|---|
| D348,930 S | 7/1994 | Olson | |
| 5,334,193 A | 8/1994 | Nardella | |
| 5,496,312 A * | 3/1996 | Klicek | 606/34 |
| 5,554,172 A * | 9/1996 | Horner et al. | 607/88 |
| 5,558,671 A * | 9/1996 | Yates | 606/38 |
| D384,413 S | 9/1997 | Zlock et al. | |
| 5,697,925 A | 12/1997 | Taylor | |
| 5,733,281 A | 3/1998 | Nardella | |
| 5,762,609 A * | 6/1998 | Benaron et al. | 600/473 |
| 5,868,737 A | 2/1999 | Taylor et al. | |
| 5,893,848 A * | 4/1999 | Negus et al. | 606/41 |
| 5,931,836 A | 8/1999 | Hatta et al. | |
| D424,694 S | 5/2000 | Tetzlaff et al. | |
| D425,201 S | 5/2000 | Tetzlaff et al. | |
| 6,113,592 A | 9/2000 | Taylor | |
| D449,886 S | 10/2001 | Tetzlaff et al. | |
| 6,322,558 B1 | 11/2001 | Taylor et al. | |
| D457,958 S | 5/2002 | Dycus et al. | |
| D457,959 S | 5/2002 | Tetzlaff et al. | |
| 6,391,024 B1 | 5/2002 | Sun et al. | |
| 6,398,781 B1 | 6/2002 | Goble et al. | |
| 6,428,537 B1 | 8/2002 | Swanson et al. | |
| 6,582,427 B1 | 6/2003 | Goble et al. | |
| 6,696,844 B2 | 2/2004 | Wong et al. | |
| D493,888 S | 8/2004 | Reschke | |
| D496,997 S | 10/2004 | Dycus et al. | |
| D499,181 S | 11/2004 | Dycus et al. | |
| 6,890,331 B2 | 5/2005 | Kristensen | |
| D509,297 S | 9/2005 | Wells | |
| D525,361 S | 7/2006 | Hushka | |
| D531,311 S | 10/2006 | Guerra et al. | |
| 7,137,980 B2 | 11/2006 | Buysse et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 2003/0216663 A1 * | 11/2003 | Jersey-Willuhn et al. | 600/547 |
| 2004/0015163 A1 * | 1/2004 | Buysse et al. | 606/34 |
| 2004/0147925 A1 * | 7/2004 | Buysse et al. | 606/51 |
| 2005/0203504 A1 * | 9/2005 | Wham et al. | 606/34 |
| 2006/0224053 A1 * | 10/2006 | Black et al. | 600/310 |
| 2009/0018536 A1 | 1/2009 | Behnke | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2602517 | 7/1976 |
| DE | 2504280 | 8/1976 |
| DE | 2514501 | 10/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3423356 | 6/1986 |
| DE | 3510586 | 10/1986 |
| DE | 3612646 | 4/1987 |
| DE | 3604823 | 8/1987 |
| DE | 8712328 | 3/1988 |
| DE | 390937 | 4/1989 |
| DE | 3904558 | 8/1990 |
| DE | 3942998 | 7/1991 |
| DE | 4303882 | 8/1994 |
| DE | 4339049 | 5/1995 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19848540 | 5/2000 |
| DE | 10045375 | 10/2002 |
| DE | 20 2007 009317 | 10/2007 |
| DE | 19738457 | 1/2009 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1159926 | 12/2001 |
| EP | 1278007 | 1/2003 |
| EP | 1609430 | 12/2005 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| RU | 401367 | 11/1974 |
| SU | 166452 | 1/1965 |
| SU | 727201 | 4/1980 |
| WO | WO 00/36986 | 6/2000 |
| WO | WO 01/01847 | 1/2001 |
| WO | WO 01/54604 | 8/2001 |
| WO | WO 2005/110264 | 11/2005 |

OTHER PUBLICATIONS

U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.

(56) References Cited

OTHER PUBLICATIONS

U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: a Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" , Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.

(56) References Cited

OTHER PUBLICATIONS

Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
C. Gabriel, "Comments on 'Dielectric Properties of the Skin'", Phys. Med. Biol. 42 (1997), pp. 1671-1674.
Robert H. Cole, "Evaluation of Dielectric Behavior by Time Domain Spectroscopy. II. Complex Permittivity", The Journal of Physical Chemistry, vol. 79, No. 14, 1975 pp. 1469-1474.
Fujimoto et al., "Femtosecond Optical Ranging in Biological Systems", Optics Letters, vol. 11, No. 3, Mar. 1986 pp. 150-152.
Taroni et al. "In Vivo Absorption and Scattering Spectroscopy of Biological Tissues", The Royal Society of Chemistry and Owner Societies 2003; Photochem. Photobiol. Sci. 2003, 2 pp. 124-129.
Aamodt et al., "In Vivo Brain Tissue Water Measurement", $17^{TH}$ Southern Biomedical Engineering Conference; 1998 p. 115.
Naito et al., "In Vivo Dielectric Analysis of Free Water Content of Biomaterials by Time Domain Reflectometry", Biological Science Laboratories, Kao Corporation, 2606 Akabane, Ichikai, Haga Tochigi 321-34, Japan; Dept. of Physics, Tokai University, Hiratsuka, Kanagawa 259-12, Japan (Apr. 7, 1997) pp. 163-172.
Athey et al., "Measurement of Radio Frequency Permittivity of Biological Tissues With an Open-Ended Coaxial Line: Part I", IEEE Transactions on Microwave Theory and Techniques, vol. MTT-30, No. 1, Jan. 1982. pp. 82-86.
Athey et al., "Measurement of Radio Frequency Permittivity of Biological Tissues With an Open-Ended Coaxial Line: Part II", IEEE Transactions on Microwave Theory and Techniques, vol. MTT-30, No. 1, Jan. 1982. pp. 87-92.
Yagihara et al., "Microwave Dielectric Study on Water Structure and Physical Properties of Aqueous Systems Using Time Domain Reflectometry With Flat-End Cells", Subsurface Sensing Technologies and Applications, vol. 2, No. 1, (2001) pp. 15-30.
C. Gabriel, "The Dielectric Properties of Biological Tissues: I. Literature Survey", Phys. Med. Biol. 41 (1996) pp. 2231-2249.
C. Gabriel, "The Dielectric Properties of Biological Tissues: II. Measurements in the Frequency Range 10 Hz to 20 GHz", Phys. Med. Biol. 41 (1996) pp. 2251-2269.
C. Gabriel, "The Dielectric Properties of Biological Tissues: III. Parametric Models for the Dielectric Spectrum of Tissues", Phys. Med. Biol. 41 (1996) pp. 2271-2293.
Feldman et al., "Time Domain Dielectric Spectroscopy Study of Biological Systems", IEEE Transactions on Dielectrics and Electrical Insulation, vol. 10, No. 5, Oct. 2003, pp. 728-753.
Miura et al., "Time Domain Reflectometry: Measurement of Free Water in Normal Lung and Pulmonary Edema", American Journal Lung Cellular Molecular Physiology 276, The American Physiological Society, Bethesda MD, (1999) pp. 207-212.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.

(56) References Cited

OTHER PUBLICATIONS

Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report EP09172749.5 dated Dec. 4, 2009.
International Search Report PCT/US08/052460 dated Apr. 24, 2008.
U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

\* cited by examiner

APPARATUS, SYSTEM AND METHOD FOR MONITORING TISSUE DURING AN ELECTROSURGICAL PROCEDURE

BACKGROUND

1. Technical Field

The present disclosure relates to an apparatus, system, and method for monitoring tissue modification during an electrosurgical procedure and, more particularly, to an apparatus, system and method that utilize the reflection of electromagnetic waves from a boundary defined by one or more biological materials having different dielectric properties.

2. Description of Related Art

Electrosurgical generators are employed by surgeons in conjunction with electrosurgical instruments to perform a variety of surgical procedures. An electrosurgical generator generates and modulates electrosurgical energy which, in turn, is applied to the tissue by an electrosurgical instrument. Electrosurgical instruments may be either monopolar or bipolar and may be configured for open or endoscopic procedures.

Using electrosurgical instruments to ablate, seal, cauterize, coagulate, and/or desiccate tissue may result in some degree of "collateral tissue damage" to adjacent tissue. For example, thermal spread across adjacent tissue structure may result during any of the aforementioned electrosurgical procedures. For the purposes herein the term "thermal spread" refers generally to the heat transfer (heat conduction, heat convection or electrical current dissipation) traveling along the periphery of the electrically conductive surfaces.

Currently available systems and methods for controlling an electrosurgical generator during electrosurgery may include a clinician monitoring and adjusting, as necessary, the amount of energy delivered to a tissue site through current, voltage, impedance, and/or power measurements such that an appropriate tissue effect can be achieved at the tissue site with minimal collateral damage resulting to adjacent tissue. These systems and/or methods typically require a clinician to translate the desired tissue effect to a power setting on an electrosurgical generator and, if necessary, adjust the power setting to compensate for tissue transformations (e.g., desiccation of tissue) associated with the electrosurgical procedure such that a desired tissue effect may be achieved.

As can be appreciated, reducing thermal spread or the like during an electrosurgical procedure reduces the likelihood of unintentional or undesirable collateral damage to surrounding tissue structures which are adjacent to an intended treatment site. Controlling and/or monitoring the depth of thermal spread during an electrosurgical procedure may aid a clinician in assessing tissue modification and/or transformation during the electrosurgical procedure.

SUMMARY OF THE DISCLOSURE

The present disclosure relates to a system for monitoring and/or controlling tissue modification during an electrosurgical procedure. The system includes an electrosurgical apparatus adapted to connect to an electrosurgical generator. The electrosurgical apparatus an electrosurgical apparatus configured to transmit energy to tissue. In an embodiment, the electrosurgical device is bipolar forceps. In an alternate embodiment, the electrosurgical device is a monopolar microwave ablation device. The system includes a control system that includes one or more electromagnetic wave source configured to generate an interrogator wave of one or more frequency adjacent tissue. Located on or in operative communication with one of the pair of jaw members is one or more sensors configured to transmit and sense a reflected portion of the interrogator wave of one or more frequencies. One or more processors are operatively coupled to the control system and to the electrosurgical generator. The processor(s) is configured to control the delivery of electrosurgical energy from the electrosurgical generator to tissue based on information provided by the tissue monitoring system. The control system may be configured to control the electrosurgical generator in real-time during the electrosurgical procedure.

The control system senses transformation of tissue and is configured to cooperate with the electrosurgical generator via the processor to control the delivery of electrosurgical energy to the tissue. For example, in one embodiment, one or more sensors may be located on one of the pair of jaw members and may include a smart sensor assembly. The one or more sensors may be configured for continuous mode of operation or real-time mode of operation. The sensors may be coupled to or integrally formed with the one or more coaxial cable.

In one embodiment, one or both jaw members include one or more sensors and include one or more windows operatively coupled to and aligned with the one or more sensor.

In another embodiment, the information provided by the control system may include propagation velocity calculations and/or phase shift calculations of the reflected portion of the electromagnetic wave of one or more frequency. In yet another embodiment, the electrosurgical apparatus is operatively coupled to a coaxial cable in operative communication with the one or more sensors and configured to transmit a portion of the interrogator wave of one or more frequencies.

In still another embodiment, the control system includes a transreceiver module configured to transmit a portion of the interrogator wave of one or more frequencies. The transceiver module may use clock signals received from a time source to perform some of the operations associated with the transceiver module. The transceiver module may be configured for amplifying, filtering, and/or digitally sampling the reflected portion of the interrogator wave of one or more frequencies.

The present disclosure also provides a method for monitoring and/or controlling the delivery of electrosurgical energy to tissue during an electrosurgical procedure. The method includes the initial step of providing an electrosurgical apparatus configured to transmit energy to tissue. The method also includes the steps of: transmitting an interrogator wave of one or more frequencies therethrough from an electromagnetic interrogator wave source; directing electrosurgical energy from an electrosurgical generator through tissue held between jaw members; directing an interrogator wave of one or more frequencies into tissue; analyzing a portion of a reflection of the interrogator wave to determine dielectric boundary data; and controlling the delivery of electrosurgical energy from the electrosurgical generator to tissue based on the dielectric boundary data provided to a processor by the one or more sensors is another step of the method.

The present disclosure further provides an apparatus for monitoring and/or controlling tissue modification during an electrosurgical procedure. The apparatus includes an electrosurgical apparatus adapted to connect to an electrosurgical generator. The electrosurgical apparatus includes a pair of jaw members configured to grasp tissue therebetween and transmit an interrogator wave of one or more frequencies therethrough. The apparatus includes one or more electromagnetic wave sources configured to generate the interrogator wave of one or more frequencies adjacent tissue and in operative communication with the electrosurgical generator and the electrosurgical apparatus. One or more sensors are configured to transmit and sense a reflected portion of the interrogator wave of one or more frequencies to determine dielectric boundary data. A processor is configured to control the delivery of electrosurgical energy from the electrosurgical generator to tissue based on dielectric boundary data provided by the one or more sensors.

BRIEF DESCRIPTION OF THE DRAWING

Various embodiments of the present disclosure are described hereinbelow with references to the drawings, wherein.

DETAILED DESCRIPTION

Figure 1:
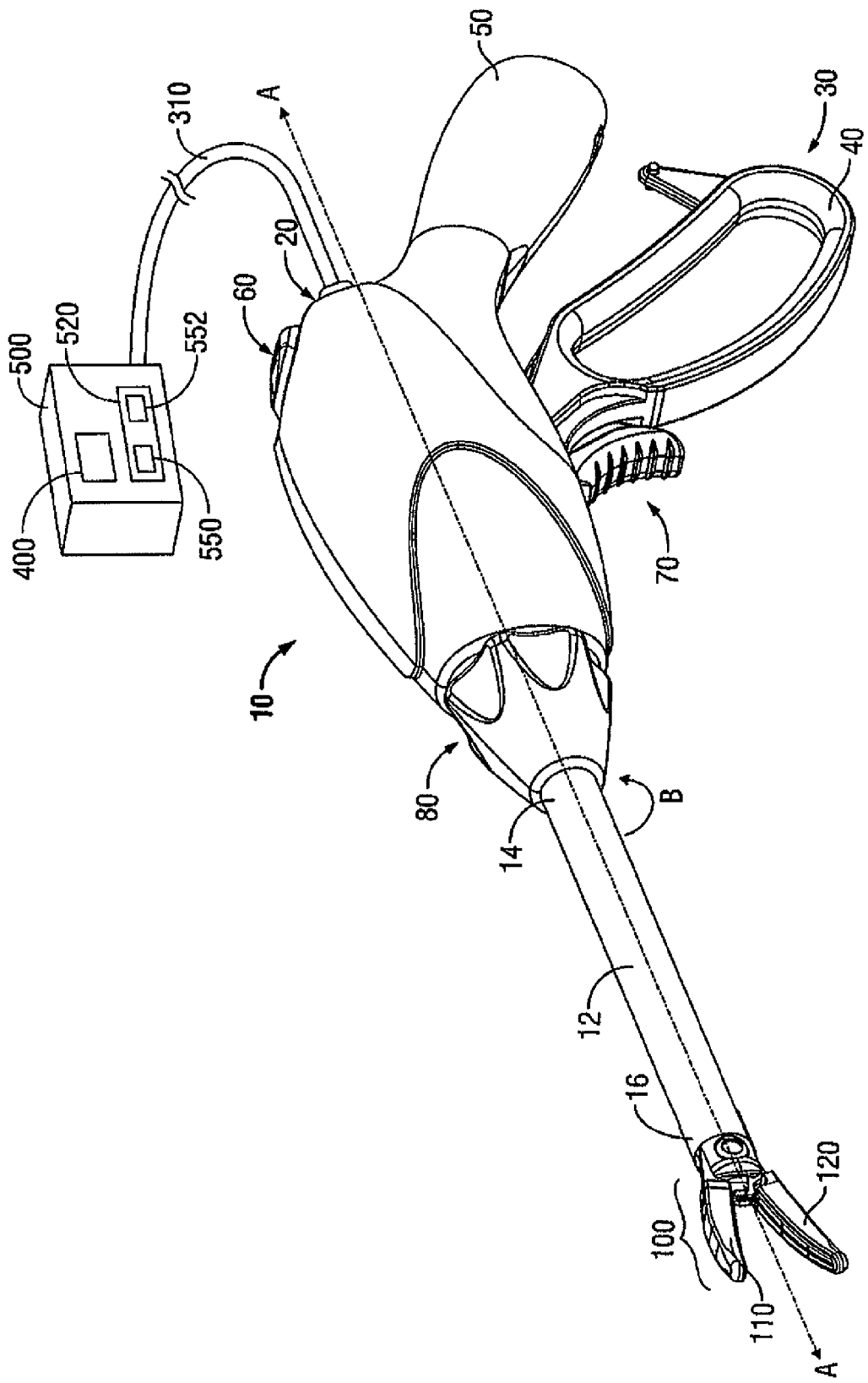
FIG. 1 is a perspective view of an endoscopic bipolar forceps and electrosurgical generator adapted for use with a system for monitoring tissue during an electrosurgical procedure according to an embodiment of the present disclosure.

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present disclosure includes an apparatus, system and method that employ principles of time domain reflectometry (TDR) to monitor tissue during various electrosurgical procedures such that a more accurate analysis of tissue reaction during the electrosurgical procedure may be obtained.

TDR involves transmission of an interrogator wave (e.g., an electromagnetic signal) thru a conductive element (e.g., a transmission line) immersed in (or otherwise in contact with) a substance of interest (e.g., biological material) while simultaneously monitoring the same conductive element for corresponding electromagnetic signals that are reflected along the conductive element. A conductive element can be understood to be any material capable of conveying electromagnetic signals. Electromagnetic signals can be reflected along the same conductive element in response to changes in the conductive element's characteristics (e.g., impedance, water content, etc.) that may be affected by substances that are in contact with the conductive element at particular locations along the conductive element's length.

As is known in the art, boundaries between biological material (e.g., muscle and membrane) having different dielectric constants can cause reflection of an incident wave as a function of the tissue properties (e.g., permittivity and conductivity). During an electrosurgical procedure the systems and/or methods of the present disclosure use reflected electromagnetic waves caused by a boundary defined by tissue having different dielectric properties to more accurately and effectively measure, amongst other things, the depth of thermal spread properties. More particularly, the present disclosure enables measuring the time period a transmitted electromagnetic wave (e.g., interrogator wave) travels from a launch point, for example, a conductive transmit element, to a boundary between tissue having different dielectric constants, and back to the launch point, the depth of the boundary of a tissue effect (e.g., thermal spread) can be measured. Additionally, the phase shift of the reflected wave may be used to determine the depth of the dielectric boundary, which, in turn, can also provide information about the depth of tissue damage.

By monitoring change in tissue properties during an electrosurgical procedure, one can better understand which tissue modifications and/or transformations lead to the best tissue effect quality. Further, and if desired, it is possible to incorporate TDR measurements into a feedback loop to facilitate in controlling electrosurgical energy delivery during an electrosurgical procedure, which, in turn, can be used to ensure that tissue modification and/or transformations are optimized.

With reference to FIG. 1, an electrosurgical apparatus 10 that is adapted for use with a control system 400 is shown. Electrosurgical apparatus 10 can be any type of electrosurgical apparatus known in the available art, including but not limited to electrosurgical apparatuses that can grasp and/or perform any of the above mentioned electrosurgical procedures. One type of electrosurgical apparatus 10 may include bipolar forceps as disclosed in United States Patent Publication No. 2007/0173814 entitled "Vessel Sealer and Divider For Large Tissue Structures". A brief discussion of bipolar forceps 10 and components, parts, and members associated therewith is included herein to provide further detail and to aid in the understanding of the present disclosure.

With continued reference to FIG. 1, bipolar forceps 10 is shown for use with various electrosurgical procedures and generally includes a housing 20, a handle assembly 30, a rotating assembly 80, a trigger assembly 70, a shaft 12, and an end effector assembly 100, which mutually cooperate to grasp, seal and divide large tubular vessels and large vascular tissues. Although the majority of the figure drawings depict a bipolar forceps 10 for use in connection with endoscopic surgical procedures, the present disclosure may be used for more traditional open surgical procedures.

Shaft 12 has a distal end 16 dimensioned to mechanically engage the end effector assembly 100 and a proximal end 14 which mechanically engages the housing 20. In the drawings and in the descriptions which follow, the term "proximal," as is traditional, will refer to the end of the forceps 10 which is closer to the user, while the term "distal" will refer to the end which is farther from the user.

Figure 2:
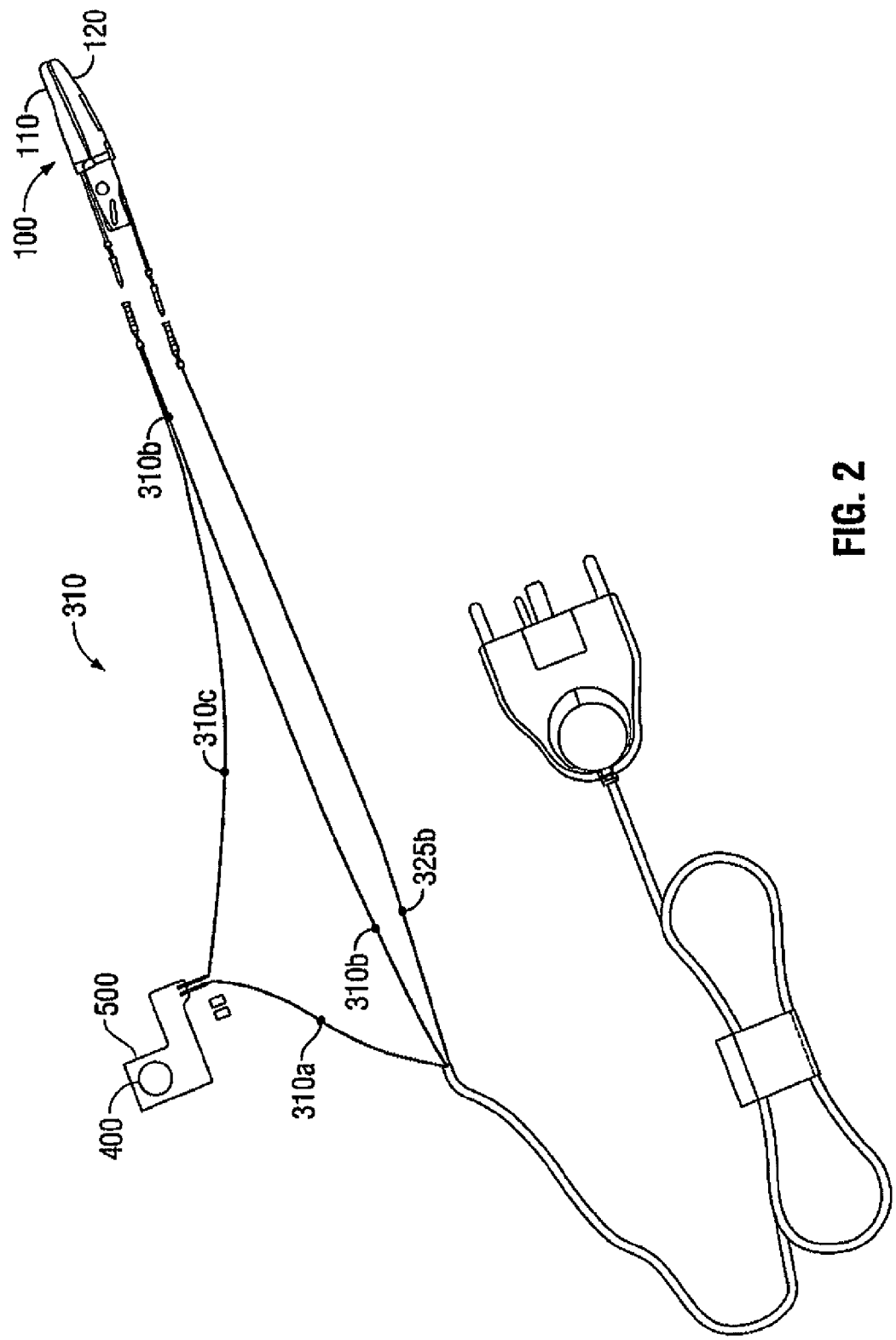
FIG. 2 is a schematic representation of an electrical configuration for connecting the endoscopic bipolar forceps to the electrosurgical generator depicted in FIG. 1.

With reference to FIGS. 1 and 2, forceps 10 includes an electrosurgical cable 310 that connects the forceps 10 to a source of electrosurgical energy, e.g., an electrosurgical generator 500, shown schematically in FIG. 1. As shown in FIG. 2, cable 310 is internally divided into cable leads 310a, 310b and 325b which are designed to transmit electrical potentials through their respective feed paths through the forceps 10 to the end effector assembly 100.

With reference again to FIG. 1, electrosurgical generator 500 (generator 500) generates electrosurgical energy, which may be RF (radio frequency), microwave, ultrasound, infrared, ultraviolet, laser, thermal energy or other electrosurgical energy. Generator 500 is operatively and selectively connected to electrosurgical apparatus 10 for performing an electrosurgical procedure. The electrosurgical procedure can include sealing, cutting, coagulating, desiccating, and fulgurating tissue; all of which may employ RF energy. Additionally, generator 500 may be configured for monopolar and/or bipolar modes of operation. Generator 500 includes all necessary components, parts, and/or members needed for system 400 to function as intended. An electrosurgical module 520 generates RF energy and includes a power supply 550 for generating energy and an output stage 552 which modulates the energy that is provided to the delivery device(s), such as the end effector assembly 100, for delivery of the modulated energy to a patient. In one embodiment, the power supply 550 may be a high voltage DC or AC power supply for producing electrosurgical current, where control signals generated by the system 400 adjust parameters of the voltage and current output, such as magnitude and frequency. The output stage 552 modulates the output energy (e.g., via a waveform generator) based on signals generated by the system 400 to adjust waveform parameters, e.g., waveform shape, pulse width, duty cycle, crest factor, and/or repetition rate. System 400 is coupled to the generator module 520 by connections that may include wired and/or wireless connections for providing the control signals to the generator module 520.

Figure 3A:
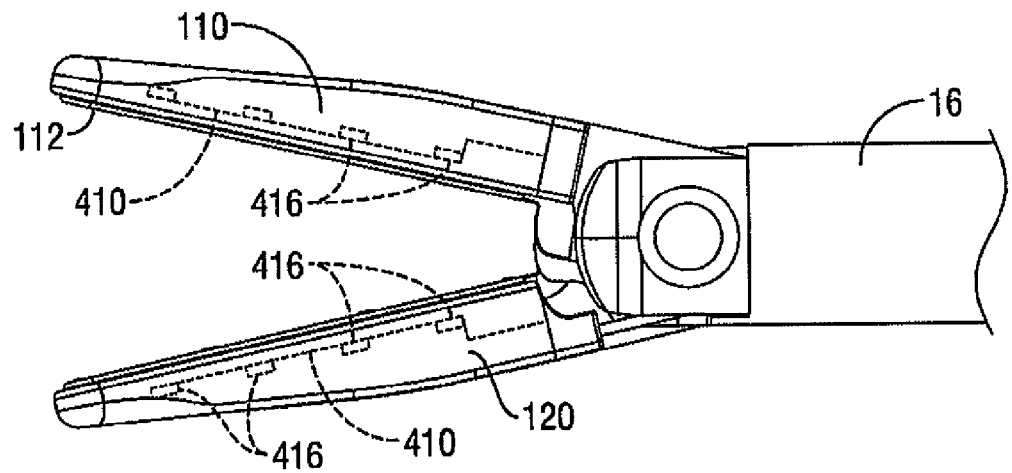
FIG. 3A is an enlarged, side view of the end effector assembly of FIG. 1.
Figure 3B:
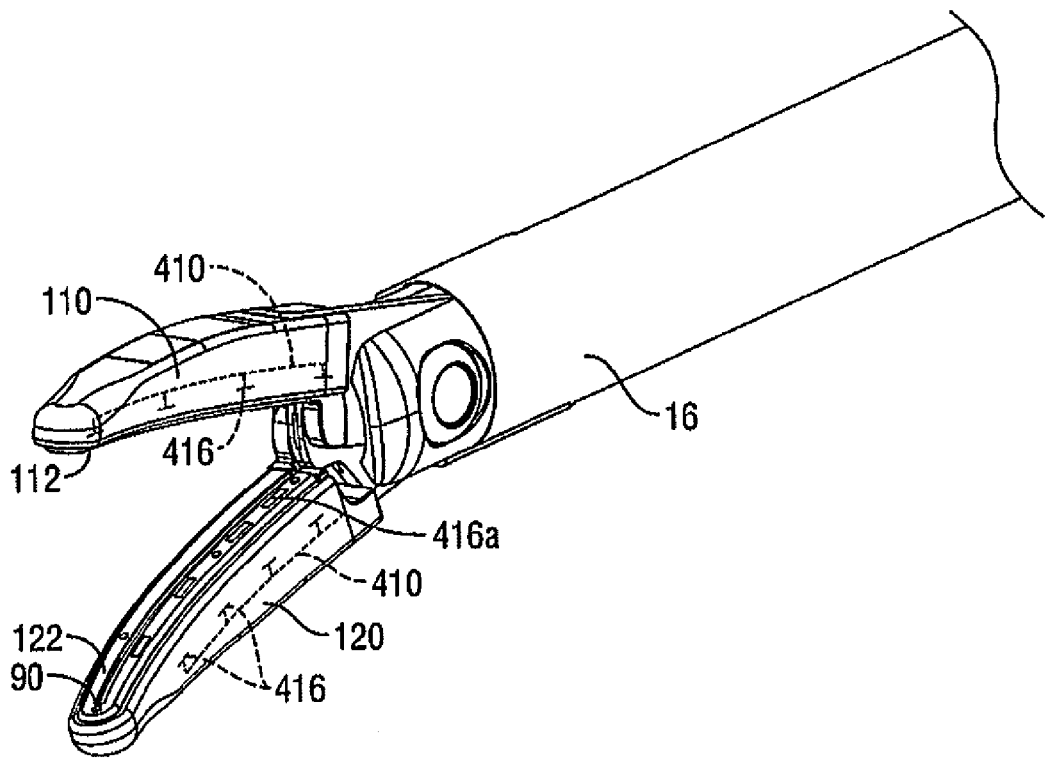
FIG. 3B is an enlarged, front perspective view of the end effector assembly of FIG. 3A shown in an open configuration.

With reference to FIGS. 3A and 3B, end effector assembly 100 is attached at the distal end 16 of shaft 12 and includes a pair of opposing jaw members 110 and 120. Movable handle 40 of handle assembly 30 is operatively coupled to a drive assembly (not explicitly shown) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Reference is made to United States Patent Publication No. 2007/0173814 for a more detailed explanation of the operation of forceps 10. A more detailed description of the functionality of system 400 now follows.

As shown, end effector assembly 100 is provided with one or more conductive transmission elements or sensors 416 in operative communication with one or more transmitters, receivers, and/or transceivers modules 406 (FIG. 4) by way of optical fiber or a cable 410. As shown, each of the jaw members includes sensors 416. Sensors 416 are placed at predetermined locations on, in, or along surfaces of jaw members 110 and/or 120, as best seen in FIGS. 3A and 3B. In embodiments, end effector assembly 100 and/or jaw members 110 and 120 may have sensors 416 placed near a proximal end and/or near a distal end of jaw members 110 and 120, as well as along the length of jaw members 110 and 120. End effector assembly 100 is also provided with one or more apertures or windows 416a. Windows 416a are configured such that sensors 416 may effectively transmit a signal and detect or sense a reflection of the signal. With this purpose in mind, windows 416a are substantially aligned with sensors 416, as best seen in FIG. 3B.

It is contemplated that one of the jaw members, e.g., jaw member 120, may include one or more sensors 416 configured to transmit an electromagnetic wave (e.g., interrogator wave) and the opposing, e.g., jaw member 10 may include a receiver configured to sense a reflection of the electromagnetic wave, or portion thereof. The electromagnetic wave may have a frequency occurring on a portion of the electromagnetic spectrum (e.g., radio frequency, microwave, visible light, and so). For illustrative purposes, sensors 416 transmit an interrogator wave occurring on the RF portion of the electromagnetic spectrum.

With reference again to FIG. 4, the system 400 for monitoring tissue during an electrosurgical procedure (e.g., RF tissue procedure) is shown. System 400 is configured to, among other things, determine the dielectric properties of a tissue of interest, such as a dielectric mismatch boundary 422. As discussed above, a dielectric mismatch boundary 422 can refer generally to a surface or region between substances that exhibits different dielectric constants. The dielectric boundary 422 can be defined by a surface or region between desiccated tissue and hydrated tissue; blood vessel and muscle; neighboring blood vessels; and a return pad and cortical bone.

System 400 includes one or more processors 402 in operative communication with a control module 404 executable on the processor 402. Control module 404 instructs a transceiver module 406 to transmit an interrogator wave or signal/pulse 408, via cable 410, to sensors 416 that contact (or are adjacent to) one or more tissue of interest "T". As shown, tissue "T" is defined by tissue segments "$T_1$" and "$T_2$". A reflection signal 412 that is a reflection of the transmitted interrogator signal 408 is detected by sensors 416 in response to the transmitted interrogator signal 408 encountering dielectric mismatch boundaries, such as the dielectric mismatch boundary 422. The reflection signal 412 is returned along cable 410 and received by a transreceiver module 406 and/or sensor module 424 and subsequently processed by the processor 402 using a time source 428 to perform, for example, propagation velocity and/or phase shift analysis between the transmitted interrogator signal 408 and the reflection signal 412.

The control module 404 processes information and/or signals (e.g., the dielectric boundary calculations input to the processor 402) and generates control signals for modulating the electrosurgical energy in accordance with the input information and/or signals. Information may include pre-surgical data (e.g., parameters of tissue, such as, for example, permittivity and/or conductivity) entered prior to the electrosurgical procedure or information entered and/or obtained during the electrosurgical procedure through sensor module 424 and/or other suitable device. The information may include requests, instructions, ideal mapping(s) (e.g., look-up-tables, continuous mappings, etc.), sensed information and/or mode selection.

The control module 404 regulates the generator 500, e.g., the power supply 550 and/or the output stage 552, which adjusts various parameters of the electrosurgical energy delivered to the patient during the electrosurgical procedure. Parameters of the delivered electrosurgical energy that may be regulated include voltage, current, resistance, intensity, power, frequency, amplitude, and/or waveform parameters, e.g., waveform shape, pulse width, duty cycle, crest factor, and/or repetition rate of the output and/or effective energy.

The control module 404 includes software instructions executable by the processor 402 for processing algorithms and/or data received by sensors 416, and for outputting control signals to the generator module 520 and/or other modules. The software instructions may be stored in a storage medium such as a memory internal to the processor 402 and/or a memory accessible by the processor 402, such as an external memory, e.g., an external hard drive, floppy diskette, CD-ROM, etc.

In embodiments, an audio or visual feedback monitor or indicator (not explicitly shown) may be employed to convey information to the surgeon regarding the status of a component of the electrosurgical system or the electrosurgical procedure. Control signals provided to the generator module 520 are determined by processing (e.g., performing algorithms), which may include using information and/or signals provided by sensors 416.

The control module 404 regulates the electrosurgical energy in response to feedback information, e.g., information related to tissue condition at or proximate the surgical site. Processing of the feedback information may include determining: changes in the feedback information; rate of change of the feedback information; and/or relativity of the feedback information to corresponding values sensed prior to starting the procedure (pre-surgical values) in accordance with the mode, control variable(s) and ideal curve(s) selected. The control module 404 then sends control signals to the generator module 520 such as for regulating the power supply 550 and/or the output stage 552.

Regulation of certain parameters of the electrosurgical energy may be based on a tissue response such as recognition of when a proper seal is achieved, when a predetermined depth of thermal spread is reached, and/or when a user is approaching a substantial or large blood vessel. Recognition of the event may automatically switch the generator 500 to a different mode of operation (e.g., coagulation mode or higher mode of operation) and subsequently switch the generator 500 back to an original mode after the event has occurred. In embodiments, recognition of the event may automatically switch the generator 500 to a different mode of operation (e.g., coagulation mode or higher mode of operation) and subsequently shutoff the generator 500.

Transceiver module 406 may be digital and/or analog circuitry that can receive instructions from and provide status to a processor 402 (via, for example, a digital-to-analog or analog-to-digital converter). Transceiver module 406 is also coupled to control module 404 to receive one or more interrogator waves 408 at a frequency and amplitude specified by the processor 402, and/or transmit the interrogator waves 408 along cable 410 to sensors 416. In one illustrative embodiment, the transceiver module 406 uses clock signals received from a pulse rate frequency clock in the time source 428 to perform at least some of its operations. Transceiver module 406 can also amplify, filter, and digitally sample the return signal 412 received by sensor 416 and transmitted along cable 410.

Time source 428 may be digital circuitry that can, for example, provide a pulse rate, variable-delayed frequency clock that operates on an equivalent time sampling detector that may be contained within a transceiver 404 and which can detect and/or be used to construct a representation of the received signal 424. In one illustrative embodiment, the time source 428 may include a delay controller, such as a voltage integrator op-amp ramp circuit with capacitor discharge reset to produce a precise linear time ramp for the delay circuit.

The sensor module 424 senses electromagnetic, electrical, and/or physical parameters or properties at the operating site and communicates with the control module 404 and/or transceiver module 406 to regulate the output electrosurgical energy. The sensor module 424 may be configured to measure, i.e., "sense", various electromagnetic, electrical, physical, and/or electromechanical conditions, such as at or proximate the operating site, including: thermal spread, tissue impedance, tissue temperature, and so on. For example, sensors of the sensor module 424 may include sensors 416 and/or other suitable sensors, such as, for example, optical sensor(s), proximity sensor(s), pressure sensor(s), tissue moisture sensor(s), temperature sensor(s), and/or real-time and RMS current and voltage sensing systems. The sensor module 424 measures one or more of these conditions continuously or in real-time such that the control module 404 can continually modulate the electrosurgical output in real-time.

Figure 4:
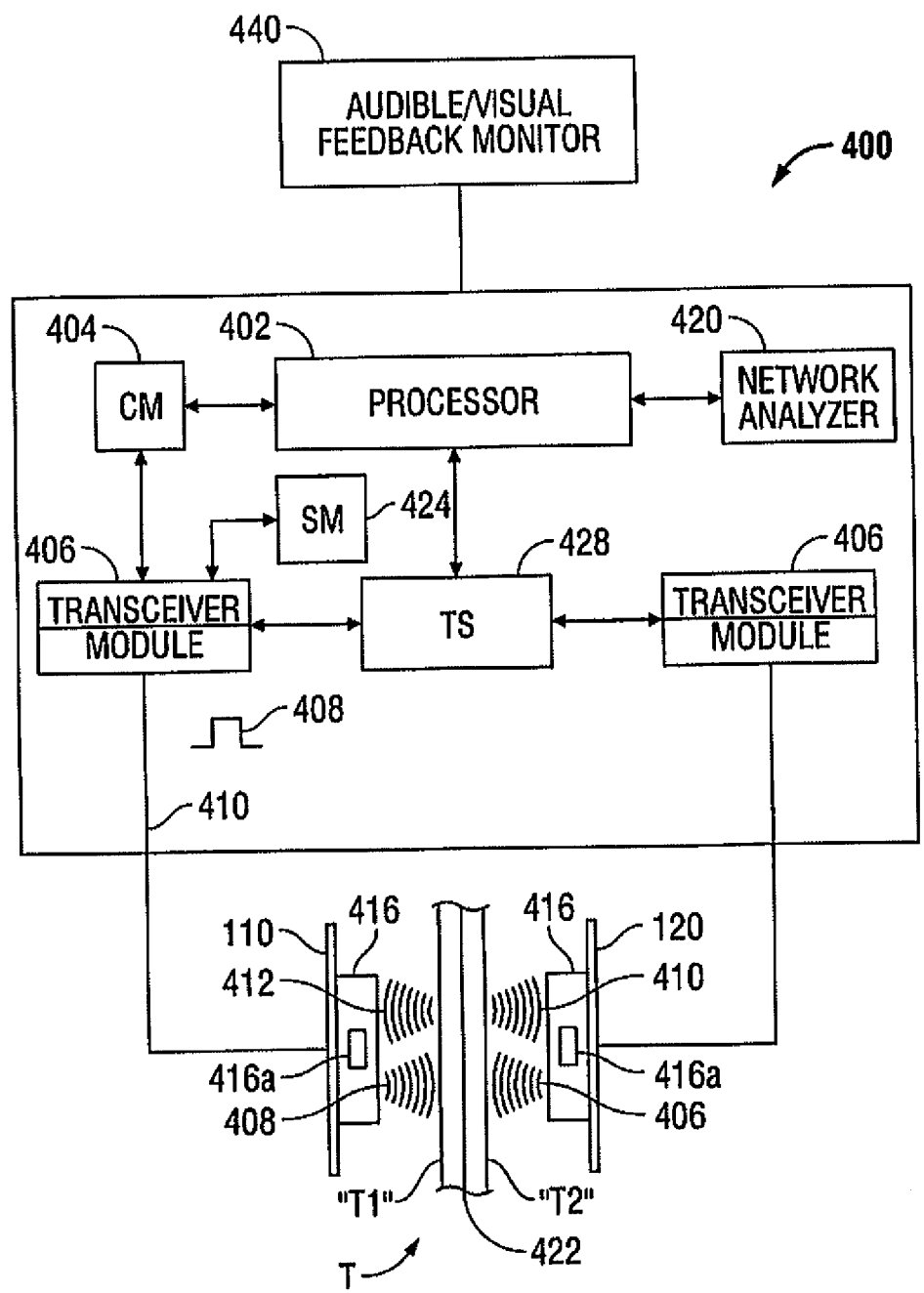
FIG. 4 is a block diagram illustrating components of the system of FIG. 1 in accordance with an embodiment of the present disclosure.

Sensors 416 are illustrated in FIG. 4 as exhibiting substantially the same characteristics (e.g., length), but those skilled in the art will recognize that their width, length, orientation, or other characteristics can vary. In one embodiment, the characteristics of each of the sensor 416 can be varied, while their transmission line impedance remains substantially constant. In another embodiment, their characteristics can be varied according to a predetermined arrangement for impedance matching and/or to obtain a desirable signal response (e.g., a coupled return at a predetermined point on the sensor that can serve as a point of reference). Sensors 416 may be separate structure coupled to a distal end of cable 410, or sensors 416 may be integrally formed at a distal end of cable 410 and configured for transmitting and sensing a reflection 412 of the transmitted signal 408.

In embodiments, sensor 416 includes a smart sensor assembly 416a (e.g., a smart sensor, smart circuit, computer, and/or feedback loop, etc.). For example, the smart sensor assembly 416a may include a feedback loop which indicates when a tissue seal is complete based upon one or more of the following parameters: depth of thermal spread, tissue temperature, tissue impedance at the seal, change in impedance of the tissue over time and/or changes in the power or current applied to the tissue over time. An audible or visual feedback monitor 440 may be employed to convey information to the surgeon regarding the overall seal quality or the completion of an effective tissue seal.

Cable 410 and/or sensors 416 may be any suitable structure suitable for carrying an electromagnetic signal, including but not limited to coaxial-arranged conductors, one or more twisted wires, fiber optics, dielectric rods, microstrip lines, coplanar striplines, coplanar waveguides, and so forth. Cable 410 operatively connects sensor 416 to one or modules of system 400. Cable 410 may follow substantially the same path as cable feed 310 and may extend within jaw members 110 and/or 120.

With continued reference to FIG. 4, system 400 is configured to analyze one or more properties associated with the reflection and transmission of an interrogator wave, for example, "time of flight" or propagation velocity measurements and/or phase shift measurements. System 400 includes any suitable analysis device for analyzing the reflected signal 412 and/or transmitted interrogator wave 408. For example, system 400 may include optical spectrum analyzers (e.g., analog and digital spectrum analyzers), network analyzers 420, Fabry-Perot interferometers, dispersive spectrometers, or any combination of analysis devices thereof.

System 400 is in operative communication with one or more network analyzers 420. Network analyzer 420 may be a Scalar Network Analyzer (SNA), which measures amplitude properties, or a Vector Network Analyzer (VNA), which measures both amplitude and phase properties. Network analyzer 420 may be configured to determine the dielectric properties of tissue.

As noted above, biological materials with different dielectric constants cause reflection of interrogator waves incident thereto as a function of the material properties. As further noted above, control module 404 processes information and/or signals (e.g., the dielectric boundary calculations input to the processor 402) and generates control signals for modulating the electrosurgical energy in accordance with the input information and/or signals. One or more control algorithms use the below formulas to calculate the reflection coefficient. The calculated reflection coefficient is processed by the control module 404 and is executable by the processor 402 for subsequent use at a latter time. For perpendicular incidence the magnitude of the reflection coefficient Γ is given by the equation:

$$\Gamma = \frac{\eta_2 - \eta_1}{\eta_2 + \eta_1} \qquad (1)$$

where η is the wave impedance which is given by the equation:

$$\eta = \sqrt{\frac{j\omega\mu}{\sigma + j\omega\varepsilon}} \qquad (2)$$

where ω is the angular velocity, μ is the magnetic permeability, σ is the electrical conductivity, and ∈ is the permittivity. For biological materials, the permittivity and conductivity are both functions of frequency.

Figure 5:
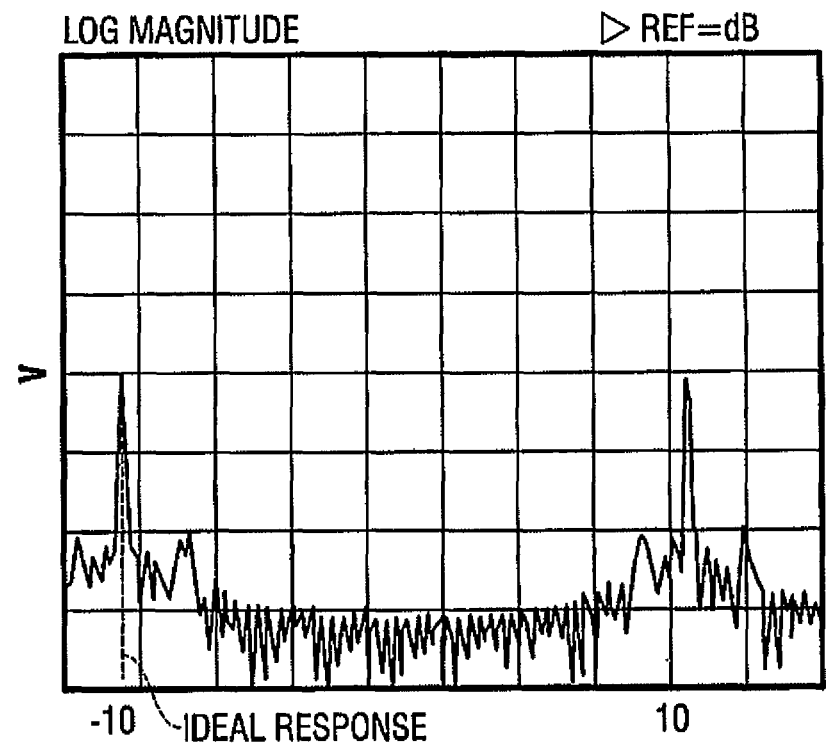
FIG. 5 is a graph showing a Time Domain Reflectometry output as viewed on a spectrum analyzer depicted in FIG. 4.

As indicated in FIG. 5, the magnitude of the reflections of interrogator waves is shown as peaks in the signal at specific frequencies. With knowledge of the permittivity ∈, the permeability μ, and the conductivity σ for selected tissue types, system 400 determines the distance from sensor 416 to the dielectric boundary 422 that causes the reflection signal 412 of the transmitted interrogator wave 408 such that tissue modifications during electrosurgical procedures may be controlled and/or monitored.

Control module 404 determines the specific frequency that maximizes the reflection coefficient Γ for selected tissue types. Here, one or more algorithms under the control of processor 402 use the following equation to predict dielectric behavior over a wide frequency range:

$$\hat{\varepsilon}(\omega) = \varepsilon_\infty + \sum_n \frac{\Delta\varepsilon_n}{1 + (j\omega\tau_n)^{(1-\alpha_n)}} + \frac{\sigma_1}{j\omega\varepsilon_0} \qquad (3)$$

where $\in_\infty$ is permittivity at frequencies where ωτ>>1 and Δ∈ is the difference between $\in_\infty$ and $\in_s$ (the permittivity at ωτ<<1). The values for τ are time constants and α is a distribution constant. Experimental data from selected tissue types provides values for the above parameters. Using the continuous data supplied by equation (3) and experimental data preloaded into one or more memory of the control module 404 and executable by the processor 402, the frequency corresponding to the highest or maximum reflection coefficient Γ is determined.

In a first application, the maximum reflection coefficient Γ for a boundary defined by desiccated tissue on a background of hydrated tissue is determined. In this application, dry tissue, which has low moisture content, is used as an analog for the desiccated tissue. In the following example, water content drives the dielectric behavior of tissue.

Figure 6:
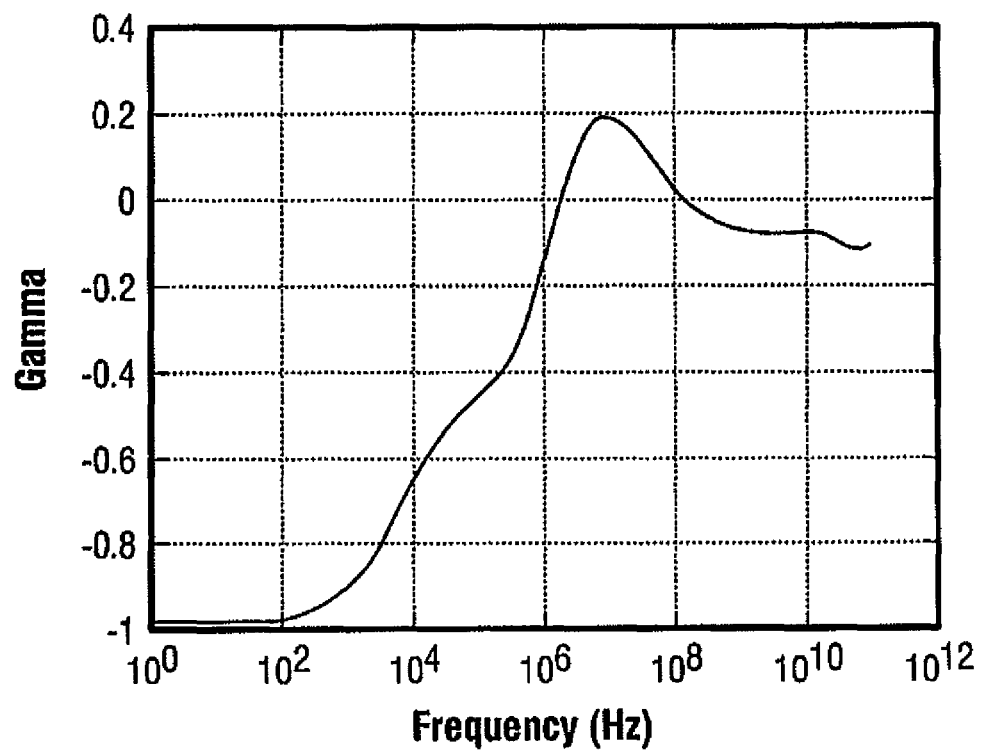
FIG. 6 is a graph showing a reflection coefficient as dependent on frequency defined by a dry skin-muscle boundary.

With reference to FIG. 6, a graph of the reflection coefficient Γ vs. frequency for a boundary defined by dry skin and hydrated tissue (e.g., muscle) is shown. As evidenced by the graph, the only non-negative values for the reflection coefficient Γ are between $2.0\times10^6$ and $1.4\times10^8$ Hz. Thus, the maximum value for Γ is 0.1856 at a frequency of $9.6\times10^6$ Hz.

In a second application, the maximum reflection coefficient Γ for a boundary defined by muscle to blood (e.g., approaching a blood vessel) is determined.

Figure 7:
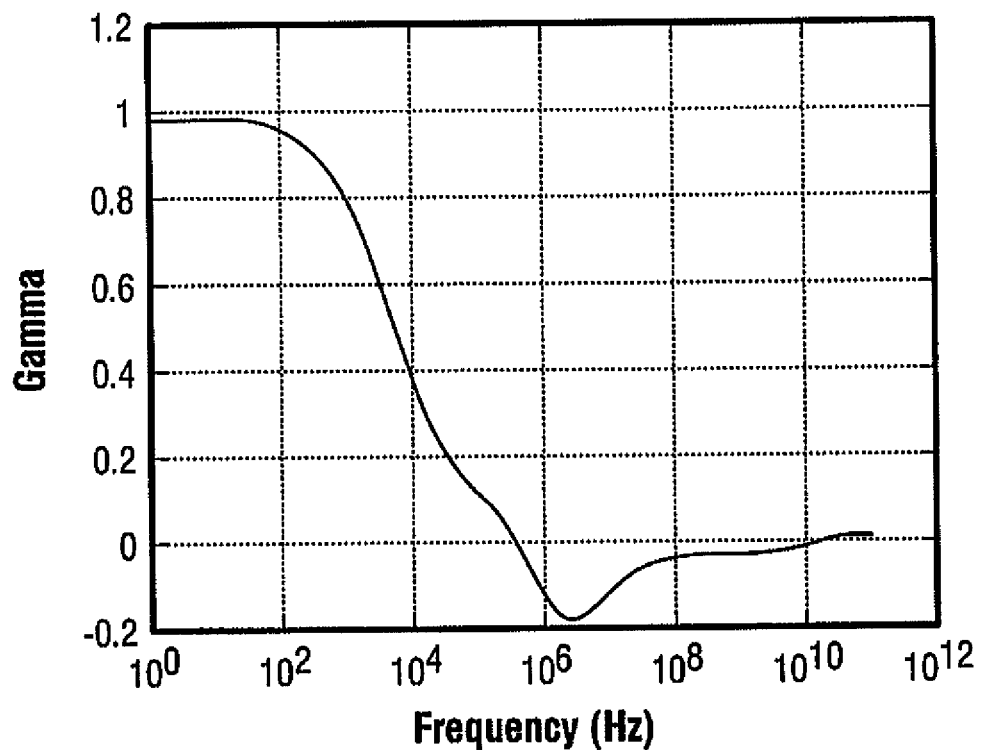
FIG. 7 is a graph showing a reflection coefficient as dependent on frequency defined by a muscle-blood boundary.

With reference to FIG. 7, a graph of the reflection coefficient Γ vs. frequency for a boundary defined by muscle and blood is shown. As evidenced by the graph, the only non-negative values for the reflection coefficient Γ are at frequencies below $3.8\times10^5$ Hz with maximum values of Γ of 0.9721 at 1 Hz; however, because electrical stimulation of tissue may cause neuromuscular stimulation at low frequencies (e.g., frequencies below $1.0\times10^4$ Hz), a lower limit for selecting an integration frequency will be set at $1.0\times10^4$ Hz. Thus, at $1.0\times10^4$ Hz the reflection coefficient Γ is 0.3792.

In a third application, the maximum reflection coefficient Γ for a boundary defined by liver and blood is determined. Using the same justification as for the muscle to blood interrogation frequency selection, an integration frequency has a lower limit of $1.0\times10^4$ Hz.

Figure 8:
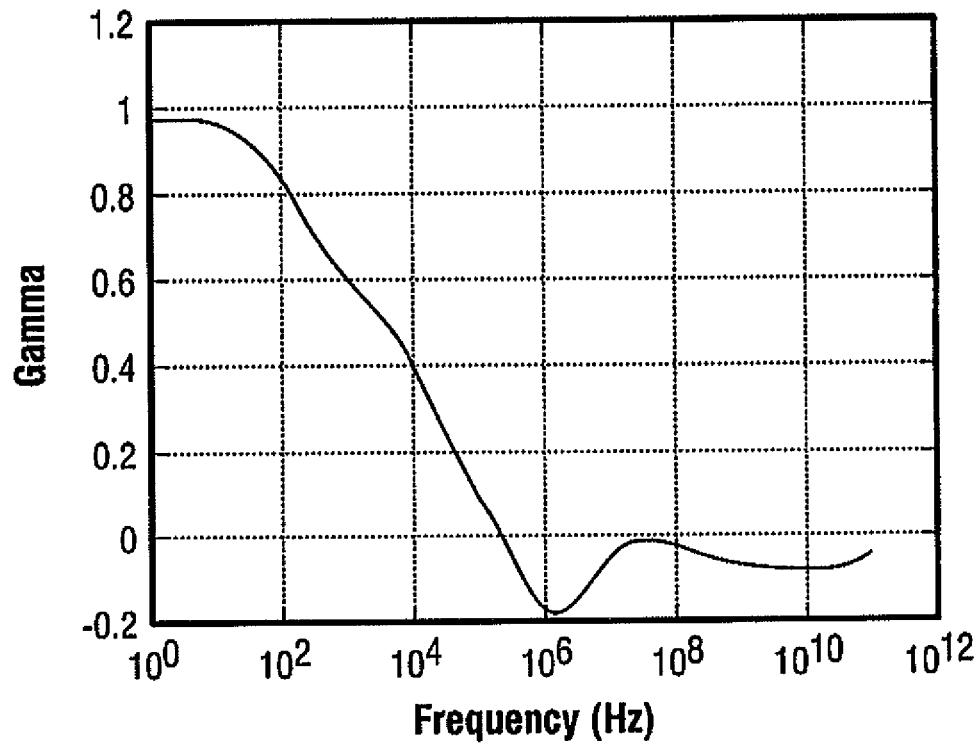
FIG. 8 is a graph showing a reflection coefficient as dependent on frequency defined by liver-blood boundary.

With reference to FIG. 8, a graph of the reflection coefficient Γ vs. frequency for a boundary defined by liver and blood is shown. As shown by the graph, the only non-negative values for the reflection coefficient Γ are at frequencies lower than $2.2\times10^5$ Hz. At an interrogation frequency of $1.0\times10^4$ the reflection coefficient is 0.4026.

In a fourth application, the maximum reflection coefficient Γ for a boundary defined by muscle tissue to cortical bone is determined. Using the same justification as for the muscle to blood, and liver and blood interrogation frequency selections, an integration frequency having a lower limit of $1.0\times10^4$ Hz is set.

Figure 9:
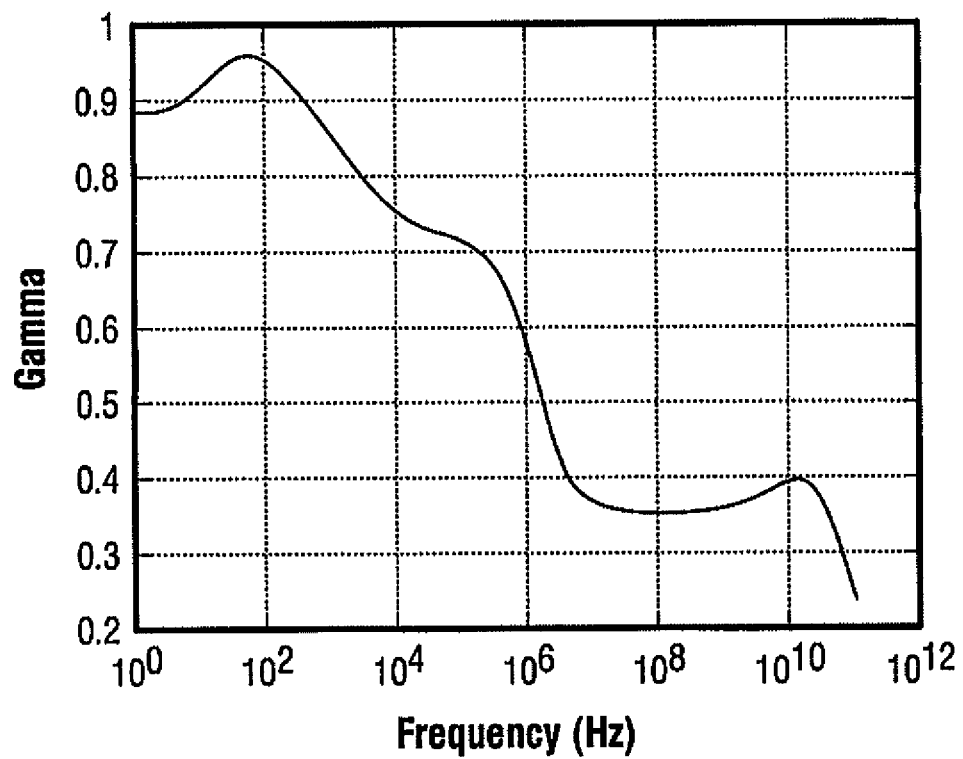
FIG. 9 is a graph showing a reflection coefficient as dependent on frequency defined by a muscle-bone boundary.

With reference to FIG. 9, a graph of the reflection coefficient Γ vs. frequency for a boundary defined by muscle and bone is shown. As shown by the graph, the reflection coefficient Γ at an interrogation frequency of $1.0\times10^4$ is 0.7515.

Electromagnetic waves propagate through homogenous medium at a speed defined by the following equation:

$$v = \frac{c}{n} \qquad (4)$$

where c is the speed of light and n is the index of refraction defined by the equation:

$$n = \sqrt{\frac{\varepsilon\mu}{\varepsilon_0\mu_0}} \qquad (5)$$

where all variables use previously described definitions. Because biological material has a magnetic permittivity of free space, equation (5) may be replaced by the approximation defined by equation:

$$n \approx \sqrt{\in_r} \qquad (6)$$

where $\in_r$ is the relative permittivity.

Using equations (4) and (6) along with the continuous data provided by equation (3), control module 404 determines the propagation velocity of the reflection signal 412 for a given dielectric boundary as a function of frequency.

Data calculated from any of the aforementioned equations is stored into a memory and accessible by one or more of the previously described modules and/or processors such that real-time or continuous data calculations may be performed.

Thus, for a given dielectric boundary where the maximum reflection coefficient Γ at a specific frequency is known, time measurements taken of a reflection signal 412 for a given transmitted interrogator wave 408 allow any of the aforementioned modules and/or processors to manipulate one or more control algorithms to calculate the distance from one or more sensors 416 to the dielectric boundary 422 such that tissue transformation during an electrosurgical procedure can be controlled and/or monitored.

Operation of system 400 is now described in terms of use with bipolar forceps 10. In the following example, thermal spread of tissue during a sealing process is monitored such that the depth of the desiccation of tissue during the electrosurgery can be determined.

In an illustrative operation and with reference again to FIG. 4, a processor 402 can instruct a transceiver module 406 to generate an interrogator wave of interest 408. In response to the processor instructions, the transceiver module 406 can access a pulse rate frequency clock associated with time source 428 to form an interrogator wave 408 exhibiting the attributes (e.g., amplitude and frequency) specified by the processor 402 and can transmit such wave 408 on one or more cables 410 to sensor 416. In another embodiment, the processor does not specify attributes of the interrogator wave 408, but rather instructs/triggers other circuitry to form the electromagnetic signal 408 and/or performs timing measurements on signals conditioned and/or filtered by other circuitry.

The transmitted interrogator 408 (e.g., one or more electromagnetic signal/pulses) travels along cable 410 to sensor(s) 416 that is/are in contact with, and/or otherwise adjacent to tissue. The transmitted interrogator wave 408, or portion thereof, is reflected from the tissue "T" as a result of the dielectric mismatch boundaries 422, that is, the boundary between dry desiccated tissue and hydrated tissue. The reflected signal 412, or portion thereof, is detected by sensors 416 and, under the control of the processor 402 the reflected signal 412 can be sampled by the transceiver module 406 and/or sensor module 424 using a controlled time delay of the pulse rate frequency clock of the time source 428 to form a representation of the reflected signal 412. The reflected signal and/or the representation of the reflected signal can also be amplified to increase the amplitude of the signal and/or filtered to remove harmonics and other interfering signals, such as signals from parasitic coupling between the transceiver-side circuitry located on a common printed circuit board, signals coupled from reflections on the sensors 416, and so forth.

The amplified and filtered reflection signal 412 can be processed by the processor 402 and/or transceiver module 404 relative to the transmitted signal 406 to determine attributes (e.g., propagation velocity measurements and/or phase shift) that can be used to derive characteristics (e.g., level and/or volume of thermal spread) associated with the tissue "T" that formed the dielectric mismatch boundary 422. The processor 402 can subsequently transmit and/or otherwise communicate the attributes of the return signal and/or the characteristics of the tissue "T" to control module 404 such that output power from generator 500 may be adjusted accordingly. The processor 402 can also subsequently transmit and/or otherwise communicate the attributes of the return signal and/or the characteristics of the tissue "T" to a local digital data processing device, a remote digital data processing device, an LED display, a computer program, and/or to any other type of entity (none of which being explicitly shown) capable of receiving the attribute and/or characteristic information.

From the foregoing and with reference to the various figure drawings, those skilled in the art will appreciate that certain modifications can also be made to the present disclosure without departing from the scope of the same. For example, it may be preferable to have sensors 416 and/or any optical fiber or cable 410 associated therewith, proximally located, and operatively and selectively connected to an electrosurgical apparatus 600; this, of course, will depend on the contemplated needs of a user. Having the sensor 416 configured in such a manner may prove useful during microwave ablation procedures.

Figure 10:
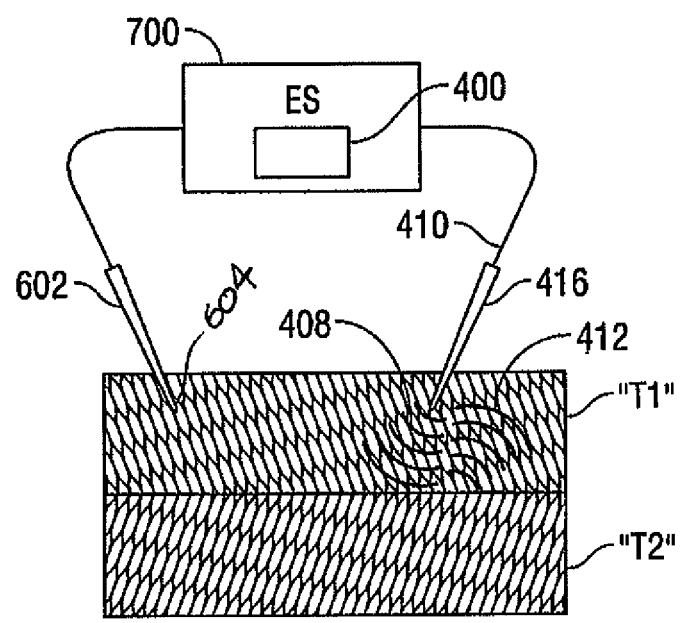
FIG. 10 is a system for monitoring tissue during an electrosurgical procedure according to an embodiment of the present disclosure.

FIG. 10 illustrates system 400 configured for use with an alternative electrosurgical apparatus 602 (e.g., monopolar apparatus configured for use with a microwave ablation procedure). Here, sensor(s) 416 are in operative communication with a microwave generator 700 and/or microwave ablation device 602. Microwave ablation device 602 includes an active electrode 604 configured to transmit energy to tissue and in operative communication with a return pad (not explicitly shown). Sensor(s) 416 may be configured to attach adjacent to an area of tissue that is to be treated. In this instance, barring structural attributes, sensor(s) 416 is configured to function as described above.

It is further contemplated that system 400 and any members, components, and/or parts associated therewith can be activated, deactivated, and/or controlled via forceps 10, and/or electrosurgical generator 500 via any handles, switches and/or buttons associated therewith.

It is envisioned that system 400 may employ phase shift measurements instead of, or in combination with time measurements such that the depth of dielectric boundary may be determined.

Those skilled in the art will recognize that it may be difficult to characterize adjacent substances that exhibit similar dielectric constants, where such conditions could result in, for example, a relatively low amplitude in the reflected signal 412, and/or where the transmit-to-receive time between the transmitted interrogator wave 408 and reflected signal 412 is comparatively small (which may, for example, experience interference from parasitic coupling). Accordingly and optionally, the disclosed technology can include a coupler composed at least in part of a material exhibiting a comparatively high dielectric constant (e.g., ceramics, plastics, etc.), conductive properties (e.g., metals, metalized materials, ferrites, etc.), and/or other properties that can be positioned at or near the dielectric mismatch boundary and that can create a coupled return signal of substantially consistent attributes (e.g., amplitude), which is independent of the dielectric properties of the substances forming the dielectric mismatch boundary.

Figure 11:
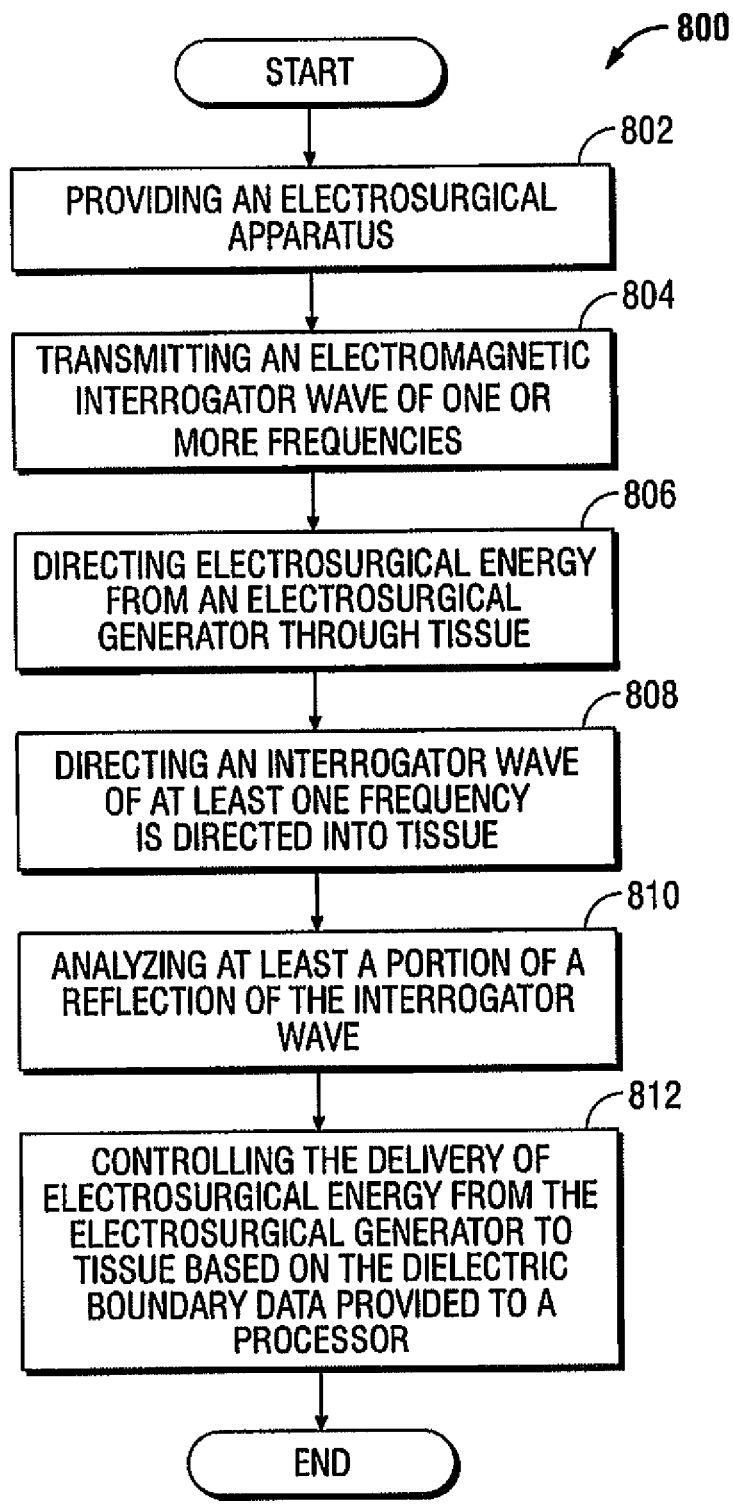
FIG. 11 is a flowchart of a method for monitoring tissue during an electrosurgical procedure according to an embodiment of the present disclosure.

FIG. 11 shows a method 800 for monitoring and/or controlling the delivery of electrosurgical energy to tissue during an electrosurgical procedure. At step 802, an electrosurgical apparatus including a pair of jaw members configured to grasp tissue therebetween and is provided. At step 804 an interrogator wave of at least one frequency from an electromagnetic interrogator wave source is transmitted through tissue. At step 806, electrosurgical energy from an electrosurgical generator is directed through tissue held between the jaw members. At step 808, the interrogator wave of one or more frequencies is directed into tissue. At step 810, at least a portion of a reflection of the electromagnetic wave is analyzed to determine dielectric boundary data. And, at step 812, the delivery of electrosurgical energy from the electrosurgical generator to tissue is controlled based on the dielectric boundary data provided to a processor.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for monitoring and/or controlling tissue modification during an electrosurgical procedure comprising:
    an electrosurgical apparatus adapted to connect to an electrosurgical generator, the electrosurgical apparatus configured to transmit energy to tissue;
    a control system including:
    at least one interrogator wave source configured to generate an interrogator wave of at least one frequency adjacent tissue;
    a sensor configured to transmit the interrogator wave of at least one frequency and sense a reflected portion of the interrogator wave of at least one frequency; and
    a processor operatively coupled to the control system and to the electrosurgical generator, the processor configured to determine a dielectric boundary data based on a phase shift between the interrogator wave of at least one frequency transmitted by the sensor and the reflected portion of the interrogator wave of at least one frequency sensed by the sensor, the processor configured to control the delivery of electrosurgical energy from the electrosurgical generator to tissue based on the dielectric boundary data determined by the processor.

2. The system according to claim 1, wherein the control system is configured to control the electrosurgical generator in real-time during the electrosurgical procedure.

3. The system according to claim 1, wherein the control system senses transformation of tissue and is configured to cooperate with the electrosurgical generator via the processor to control the delivery of electrosurgical energy to the tissue.

4. The system according to claim 1, wherein the electrosurgical apparatus includes a pair of jaw members configured to grasp tissue therebetween.

5. The system according to claim 4, wherein the sensor is located on of the pair of jaw members.

6. The system according to claim 5, wherein the sensor includes a smart sensor assembly.

7. The system according to claim 1, wherein the electrosurgical apparatus includes an active electrode in operative communication with a return electrode.

8. The system according to claim 1, wherein the information provided by the control system includes one of propagation velocity calculations and phase shift calculations of the reflected portion of the interrogator wave of at least one frequency.

9. The system according to claim 1, wherein the electrosurgical apparatus is operatively coupled to a coaxial cable in operative communication with the sensor and configured to transmit at least a portion of the interrogator wave of at least one frequency.

10. The system according to claim 1, wherein the control system includes a transceiver module configured to transmit at least a portion of the interrogator wave of at least one frequency.

11. The system according to claim 10, wherein the transceiver module uses clock signals received from a time source to perform at least some of the operations associated with the transceiver module.

12. The system according to claim 11, wherein transceiver module is configured for at least one of amplifying, filtering, and digitally sampling the reflected portion of the interrogator wave of at least one frequency.

13. The system according to claim 1, wherein the sensor is configured for continuous mode of operation.

14. The system according to claim 1, wherein the sensor is configured for real-time mode of operation.

15. The system according to claim 9, wherein the sensor is coupled to the at least one coaxial cable.

16. The system according to claim 9, wherein the sensor is integrally formed with the at least one coaxial cable.

17. The system according to claim 4, wherein at least one jaw member includes the sensor and includes at least one window operatively coupled to and aligned with the sensor.

18. A method for monitoring and/or controlling the delivery of electrosurgical energy to tissue during an electrosurgical procedure comprising the steps of:
    providing an electrosurgical apparatus configured to apply energy to tissue;
    transmitting through a sensor an interrogator wave of at least one frequency therethrough from an electromagnetic interrogator wave source;
    directing at the sensor the interrogator wave of at least one frequency into tissue;
    sensing a reflected portion of the interrogator wave of at least one frequency from the tissue with the sensor;
    analyzing the sensed reflected portion of the interrogator wave of at least one frequency to determine a dielectric boundary data based on a phase shift between the interrogator wave of frequency and the sensed reflected portion of the interrogator wave of at least one frequency; and
    controlling the delivery of electrosurgical energy from the electrosurgical generator to tissue based on the determined dielectric boundary data.

19. The method of claim 18, wherein the step of analyzing includes the step of calculating the maximum reflection coefficient of the interrogator wave of at least one frequency.

20. The method of claim 18, wherein the step of analyzing includes the step of calculating the propagation velocity of the at least a portion of the reflection of the interrogator wave.

21. The method of claim 18, wherein the step of controlling the delivery of electrical energy includes at least one of reducing, increasing and stopping electrosurgical energy delivery.

22. An apparatus for monitoring and/or controlling tissue modification during an electrosurgical procedure comprising:
    an electrosurgical apparatus adapted to connect to an electrosurgical generator, the electrosurgical apparatus configured to apply energy to tissue;
    at least one electromagnetic wave source configured to generate an interrogator wave of at least one frequency adjacent tissue and in operative communication with the electrosurgical generator and the electrosurgical apparatus;
    a sensor configured to transmit the interrogator wave of at least one frequency and sense a reflected portion of the interrogator wave of at least one frequency; and
    a processor operatively coupled to the electromagnetic wave source and to the electrosurgical generator, the processor configured to determine a dielectric boundary data based on a phase shift between the interrogator wave of at least one frequency transmitted by the sensor and the reflected portion of the interrogator wave of at least one frequency sensed by the sensor, the processor configured to control the delivery of electrosurgical energy from the electrosurgical generator to tissue based on the dielectric boundary data determined by the processor.

* * * * *